(12) United States Patent
Dou

(10) Patent No.: US 11,684,372 B2
(45) Date of Patent: Jun. 27, 2023

(54) INTELLIGENT FEMORAL ARTERY HEMOSTASIS DEVICE BY COMPRESSION

(71) Applicant: Henan Junankang Medical Equipment Sales Co., Ltd, Xinzheng (CN)

(72) Inventor: Zhigang Dou, Henan (CN)

(73) Assignee: Henan Junankang Medical Equipment Sales Co., Ltd, Xinzheng (CN)

( * ) Notice: Subject to any disclaimer, the term of this patent is extended or adjusted under 35 U.S.C. 154(b) by 590 days.

(21) Appl. No.: 16/871,944

(22) Filed: May 11, 2020

(65) Prior Publication Data

US 2021/0177431 A1 Jun. 17, 2021

(30) Foreign Application Priority Data

Dec. 12, 2019 (CN) .......................... 201922221748.5

(51) Int. Cl.
*A61B 17/132* (2006.01)
*A61B 17/00* (2006.01)

(52) U.S. Cl.
CPC . *A61B 17/1325* (2013.01); *A61B 2017/00119* (2013.01); *A61B 2017/00199* (2013.01); *A61B 2560/029* (2013.01)

(58) Field of Classification Search
CPC ..... A61F 5/30; A61F 5/32; A61F 5/34; A61B 5/6822; A61B 5/6823; A61B 5/6825; A61B 5/6826; A61B 5/6828; A61B 5/6829; A61B 17/132; A61B 17/1325; A61B 17/1327; A61B 17/135; A61B 17/1355; A61B 2560/029

See application file for complete search history.

(56) References Cited

U.S. PATENT DOCUMENTS

| | | | | |
|---|---|---|---|---|
| 37,156 A | * | 12/1862 | Dunton | A61B 17/1327 606/203 |
| 1,281,653 A | * | 10/1918 | Plummer | A61B 17/1327 606/203 |
| 3,050,064 A | * | 8/1962 | Moore | A61F 13/10 606/203 |

(Continued)

FOREIGN PATENT DOCUMENTS

CN 110025354 A 7/2019

*Primary Examiner* — Darwin P Erezo
*Assistant Examiner* — Christian D Knauss

(57) ABSTRACT

Disclosed is an intelligent femoral artery hemostasis device by compression, including a main body capable of automatic compression. The main body includes a compression mechanism and a pressing plate mechanism successively provided from bottom to top; a lift regulator is provided between the support column and the compression mechanism; the compression mechanism is further provided with a detector for bleeding detection; and the main body is further integrated with a power supply module, an operation module and a central processing module. This invention realizes automatic bleeding detection and automatic pressurizing, and ensures the integration and compactness of the device. The power supply module, the operation module and the central processing module are integrated in the main body, avoiding external connecting wires and making it convenient to use the device when the tourniquet works in a twining working condition.

10 Claims, 4 Drawing Sheets

(56) References Cited

U.S. PATENT DOCUMENTS

| | | | | |
|---|---|---|---|---|
| 4,036,229 | A | * | 7/1977 | Marinello ............. A61M 35/00 |
| | | | | 604/289 |
| 5,139,512 | A | * | 8/1992 | Dreiling ............. A61B 17/1325 |
| | | | | 606/217 |
| 5,554,168 | A | * | 9/1996 | Petersen ............. A61B 17/132 |
| | | | | 600/504 |
| 2011/0202089 | A1 | * | 8/2011 | Sun .................... A61B 17/1325 |
| | | | | 606/201 |
| 2013/0289614 | A1 | * | 10/2013 | Cully ................ A61B 17/1322 |
| | | | | 606/203 |

* cited by examiner

INTELLIGENT FEMORAL ARTERY HEMOSTASIS DEVICE BY COMPRESSION

CROSS-REFERENCE TO RELATED APPLICATION

This application claims the benefit of priority from Chinese Patent Application No. 201922221748.5, filed on Dec. 12, 2019. The content of the aforementioned application, including any intervening amendments thereto, is incorporated herein by reference in its entirety.

TECHNICAL FIELD

This application relates to a medical supply for femoral artery hemostasis by compression, and more particularly to an intelligent femoral artery hemostasis device by compression.

BACKGROUND OF THE INVENTION

After an interventional operation, hemostasis by compression is generally adopted. This method has the following advantages. The vascular structure is not damaged, and objects filled with gel or collagen are not required to be stitched, which shortens the hospital stay of patients. In addition, artery blood vessels can be punctured repeatedly. In the hemostasis by compression, doctors or medical professionals press at the puncture site of arterial duct, which generally includes an initial pressing and a later pressing. A higher pressure is provided for the initial pressing, after a period of time, the pressure is reduced to enter the later pressing to provide abundant blood supply to lower vascular tissues.

Chinese Patent Application No. 201910445640.6 (Henan Jun'an Kang Medical Equipment Sales Co., Ltd.), filed on May 27, 2019, discloses an automatic pressurizing femoral artery hemostasis device by compression, which includes a compression mechanism and a pressing plate mechanism successively provided from bottom to top; where the compression mechanism and the pressing plate mechanism are in a separated structure; a support column is provided on the pressing plate mechanism and extends towards the compression mechanism; a lift regulator is provided between the support column and the compression mechanism and is configured to regulate the lifting of the support column; and the compression mechanism is also provided with a detector for bleeding detection which is connected to the lift regulator for control. The above invention realizes automatic bleeding detection and automatic pressurizing, so that the bleeding is processed in real time, and complications thereof are reduced, which relieves workload of the medical staff and saves the labor cost for hospitals.

In the follow-up development, a new structure of the automatic femoral artery hemostasis device by compression is found, which realizes automatic bleeding detection and automatic compression, and ensures the integration and compactness of the device.

SUMMARY OF THE INVENTION

To solve the problems in the prior art, the invention provides an intelligent femoral artery hemostasis device by compression.

The invention adopts the following technical solutions.

The invention provides an intelligent femoral artery hemostasis device by compression, comprising a main body capable of automatic compression;

wherein the main body comprises a compression mechanism and a pressing plate mechanism successively provided from bottom to top; the compression mechanism and the pressing plate mechanism are in a separated structure; a support column is provided on the pressing plate mechanism and extends towards the compression mechanism; a lift regulator is provided between the support column and the compression mechanism and is configured to regulate the lifting of the support column; the lift regulator comprises a lift mechanism and a transmission mechanism which drives the movement of the lift mechanism; the compression mechanism is further provided with a detector for bleeding detection; and the main body is further integrated with a power supply module, an operation module and a central processing module; the detector and the operation module are respectively connected to a signal input end of the central processing module; and a signal output end of the central processing module is connected to the transmission mechanism of the lift regulator.

The operation module comprises a mainboard component arranged in the pressing plate mechanism and a control contact arranged on the mainboard component; wherein a mainboard button is partially provided outside the pressing plate mechanism and is configured to cooperate with the control contact.

The mainboard button comprises a first mainboard button for a manual mode and a second mainboard button for an automatic mode.

The compression mechanism comprises a compression block, a space from which a tourniquet passes and a space from which a fixing band passes; the space from which the tourniquet passes and the space from which the fixing band passes are provided at the compression block, and the space from which the tourniquet passes is located above the space from which the fixing band passes;

an installation chamber is provided in the compression block; a bottom surface of the compression block is provided with a compression bulge; an upper side of the compression block is provided with a hole through which the support column passes; a connecting sleeve which protrudes upwardly is provided corresponding to the hole on the compression block; the support column passes through the connecting sleeve and is connected to the lift regulator arranged in the installation chamber of the compression block; and the pressing mechanism comprises a pressing plate; and the pressing plate is connected to the support column and is provided with a space from which the tourniquet passes.

The pressing plate is a flat sleeve; a middle channel of the flat sleeve forms the space from which the tourniquet passes; an installation case is formed at an upper part of the middle channel of the pressing plate; and the power supply module, the operation module and the central processing module are located in the installation case.

The installation case is formed by a top cover and a lower casing which are detachably connected; the lower casing is fixedly connected to a lower part of the middle channel; and the mainboard button of the operation module is provided on the top cover.

The lift mechanism comprises an inner threaded hole arranged at an axis of the support column and a stud matching and arranged in the inner threaded hole, wherein a lower end of the stud is connected to the transmission mechanism in a transmission manner;

the support column has a non-circular section, so that the support column cooperates with the hole to achieve a circumferential rotation limit for the support column;

a positioning bulge is further provided on the support column; a start limit switch and an end limit switch are provided corresponding to the positioning bulge in the installation chamber; the start limit switch and the end limit switch are respectively connected to the signal input end of the central processing module;

when the positioning bulge contacts the start limit switch, a signal is sent from the start limit switch to the central processing module, and the central processing module sends out a signal to control the transmission mechanism to stop working; at this moment, the pressing plate mechanism locates at the lowest position; and when the positioning bulge contacts the end limit switch, a signal is sent from the end limit switch to the central processing module, and the central processing module sends out a signal to control the transmission mechanism to stop working; and at this moment, the pressing plate mechanism locates at the highest position.

The installation case in the pressing plate mechanism is further provided with an alarm;

the detector comprises two metal probes which are spaced and arranged at a compression position at the bottom surface of the compression block; when a puncture site is bleeding, a micro short circuit is generated between the two metal probes; the detector sends a signal to the central processing module; the central processing module sends out a signal to control the transmission mechanism to raise the support column, and the central processing module sends a signal to the alarm.

The installation case of the pressing plate mechanism is further provided with a time display module, and a display screen of the time display module is provided on the top cover of the installation case.

A wire for connecting the central processing module and the transmission mechanism and a wire for connecting the central processing module and the detector are wrapped around the support column at the connecting sleeve to form a spring wire structure.

Compared with the prior art, the invention has the following beneficial effects.

This invention realizes automatic bleeding detection and automatic pressurizing, and ensures the integration and compactness of the intelligent femoral artery hemostasis device by compression. The power supply module, the operation module and the central processing module are integrated in the main body of the femoral artery hemostasis device, avoiding external connecting wires and making it convenient to use the intelligent femoral artery hemostasis device by compression when the tourniquet works in a twining working condition.

DETAILED DESCRIPTION OF EMBODIMENTS

The invention will be described in detail below with reference to the accompanying drawings and embodiments.

Figure 1:
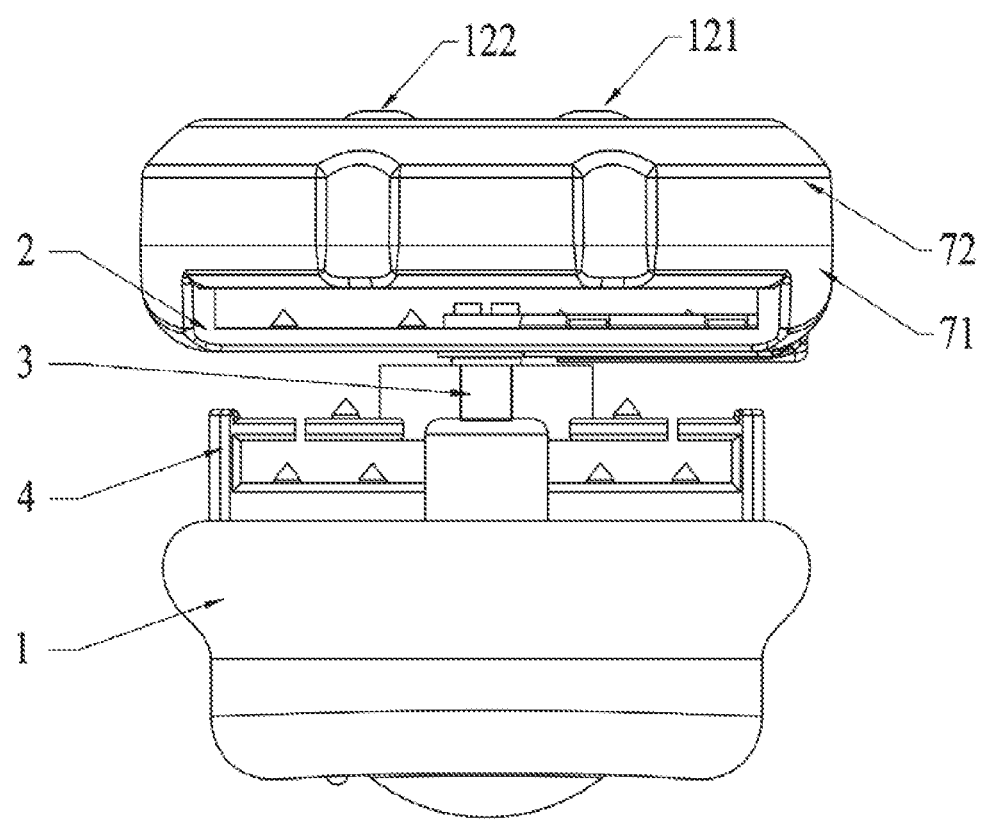
FIG. 1 is a schematic diagram of an intelligent femoral artery hemostasis device by compression in a decompression state according to the invention.
Figure 2:
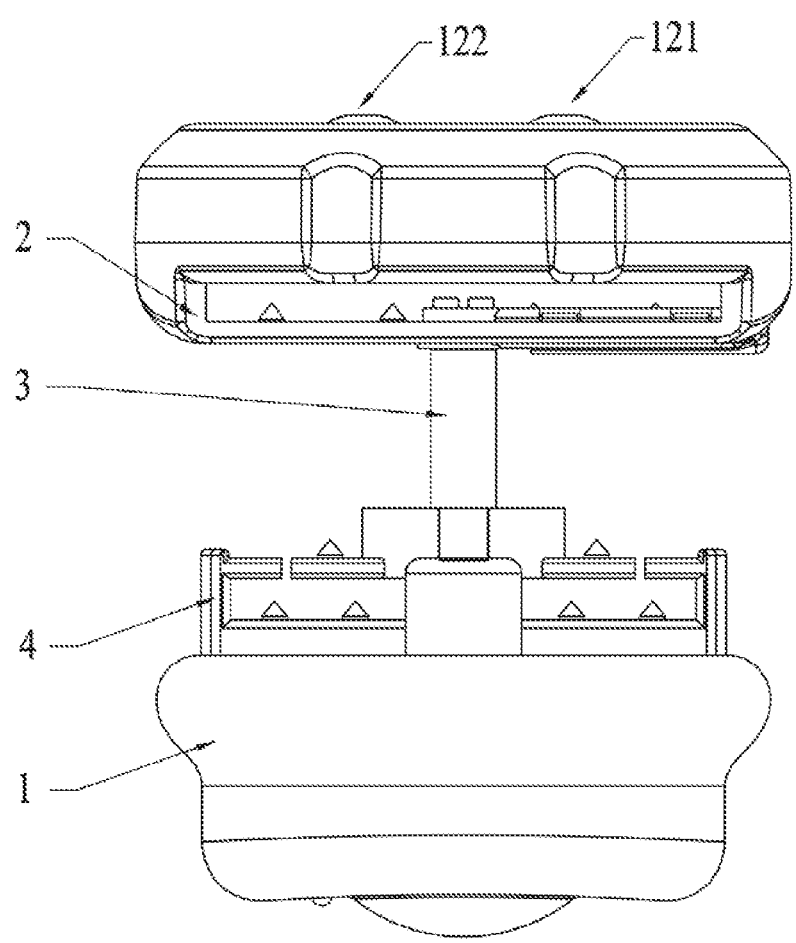
FIG. 2 is a schematic diagram of the intelligent femoral artery hemostasis device by compression in a compression state according to the invention.
Figure 3:
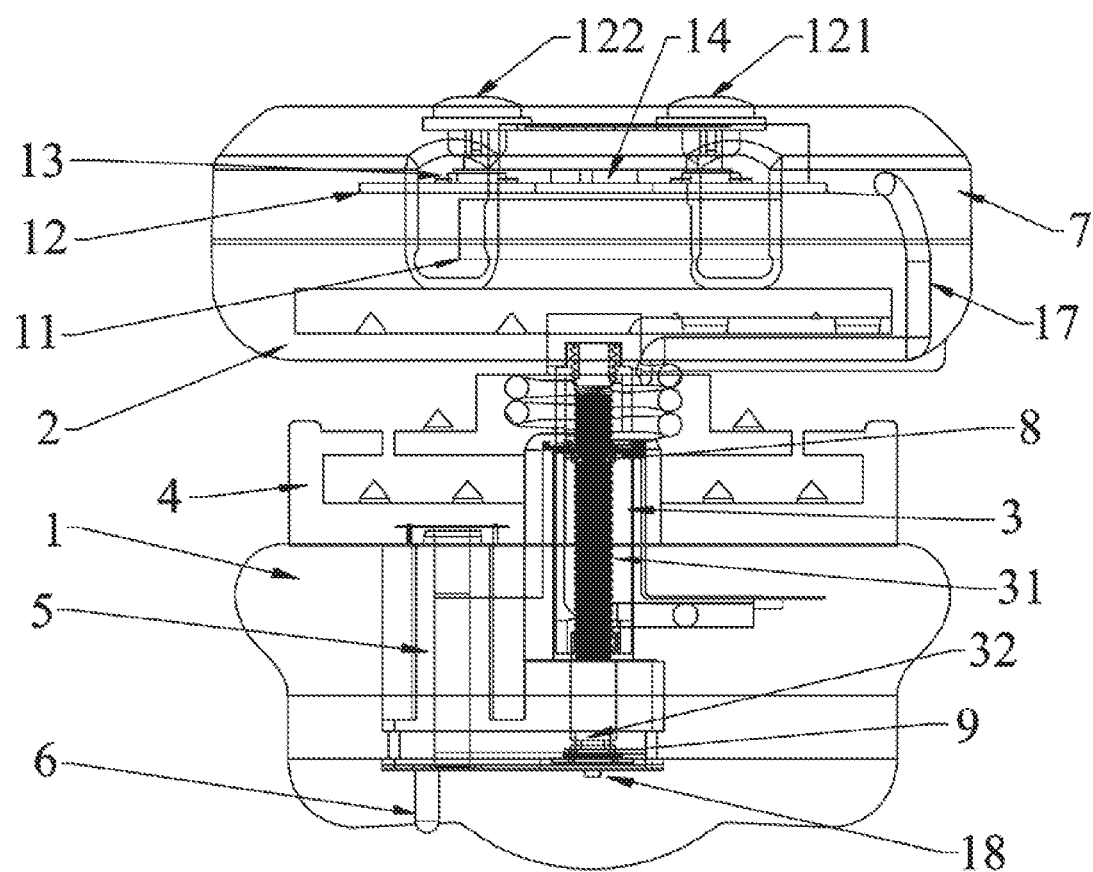
FIG. 3 schematically shows an inner structure of the intelligent femoral artery hemostasis device by compression according to the invention.
Figure 4:
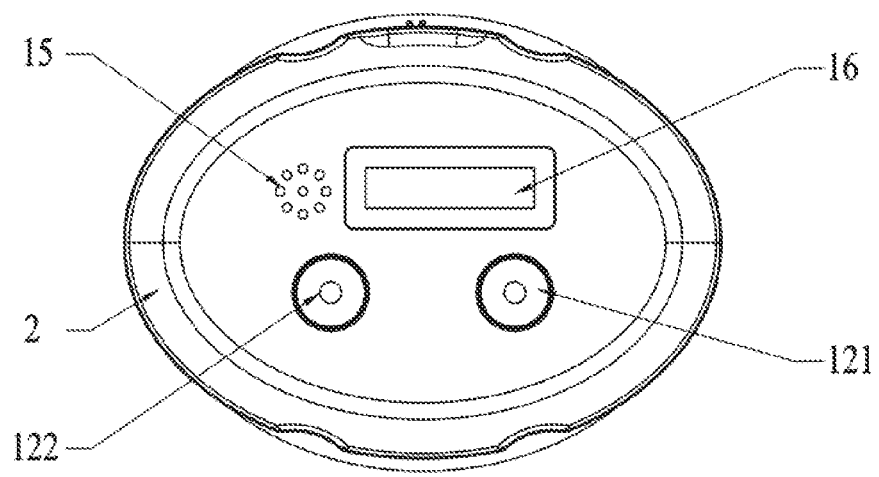
FIG. 4 is a top view of FIG. 1.
Figure 5:
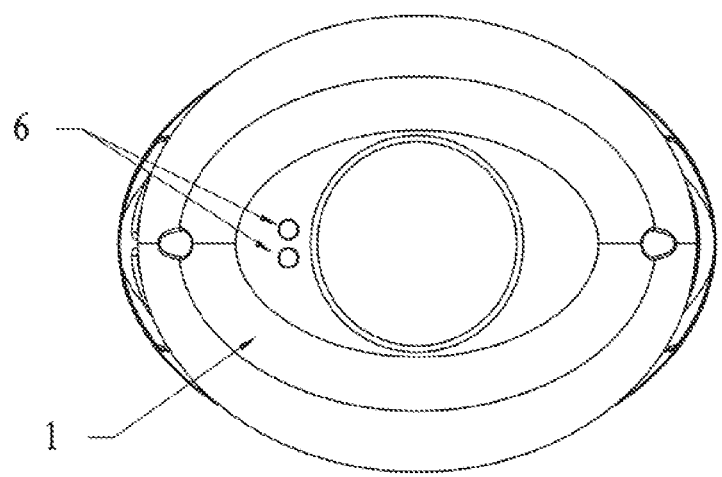
FIG. 5 is a bottom view of FIG. 2.

As shown in FIGS. 1-5, the invention provides an intelligent femoral artery hemostasis device by compression, including a main body capable of automatic compression for automatic bleeding detection and automatic pressurizing. The main body is integrated with a power supply module 11, an operation module and a central processing module 14. The power supply module 11 is a rechargeable battery and is configured to supply power for various operations of the main body.

The main body is based on the femoral artery hemostasis device by automatic compression disclosed in Chinese Patent Application No. 201910445640.6. The main body includes a compression mechanism and a pressing plate mechanism successively provided from bottom to top. The compression mechanism and the pressing plate mechanism are in a separated structure. A support column 3 is provided on the pressing plate mechanism and extends towards the compression mechanism. A lift regulator is provided between the support column 3 and the compression mechanism and is configured to regulate the lifting of the support column 3. The lift regulator includes a lift mechanism and a transmission mechanism which drives the movement of the lift mechanism.

The compression mechanism is further provided with a detector 6 for bleeding detection.

The compression mechanism includes a compression block 1, a space from which a tourniquet passes provided on the compression block 1, and a space from which a fixing band passes; where the space from which the tourniquet passes is located above the space from which the fixing band passes.

An installation chamber is provided in the compression block 1. A compression budge is provided on a bottom surface of the compression block 1 and is made of an elastic material. An upper side of the compression block 1 is provided with a hole through which the support column 3 passes. The support column 3 passes through the hole and is connected to the lift regulator arranged in the installation chamber of the compression block 1.

The support column 3 has a non-circular section, such as oval, rhombus and square, so that the support column 3 cooperates with the hole to achieve a circumferential rotation limit for the support column 3, and the axial lifting of the support column 3 is not affected.

In this embodiment, a connecting sleeve which protrudes upwardly is provided corresponding to the hole on the compression block 1, and also has a non-circular section, so that the support column 3 matches with and passes through the connecting sleeve.

A positioning card 4 is symmetrically provided at left and right sides of the connecting sleeve and on an upper side of the compression block 1. The space from which the fixing band passes is formed in the positioning card 4. The positioning card 4 is further provided with a notch through which the fixing band passes. The space from which the tourniquet passes is formed at an upper side of the positioning card 4.

The pressing mechanism includes a pressing plate 2 connected to the support column. The pressing plate 2 is a flat sleeve; a middle channel of the flat sleeve forms a space from which the tourniquet passes.

The spaces from which the tourniquet passes and the space from which the fixing band passes each are provided with an antiskid bulge. Specifically, the intelligent femoral artery hemostasis device of the invention is applied in cooperation with a bellyband which is disclosed in Chinese Patent Application No. 201510065851.9 and will not be described in detail herein. The fixing band of the bellyband passes through the space from which the fixing belt passes and is fixed at a fastener behind hip to position the compression mechanism. The tourniquet passes through the spaces from which the tourniquet passes and is pressurized and fixed at the fastener behind hip to achieve the hemostasis by compression for the bleeding point.

The detector 6 and the operation module are respectively connected to a signal input end of the central processing module 14; and a signal output end of the central processing module 14 is connected to the transmission mechanism of the lift regulator.

In this embodiment, the lift mechanism includes an inner threaded hole arranged at an axis of the support column 3 and a stud 31 matching and arranged in the inner threaded hole; and a lower end of the stud 31 is connected to the transmission mechanism in a transmission manner.

In this embodiment, the transmission mechanism includes a motor 5 arranged in the installation chamber of the compression block 1, and the motor 5 is connected to the stud 31 in a transmission manner.

In this embodiment, a positioning bulge 32 is further provided on the support column 3. A start limit switch 8 and an end limit switch 9 are provided corresponding to the positioning bulge 32 in the installation chamber. The start limit switch 8 and the end limit switch 9 are respectively connected to the signal input end of the central processing module 14.

The start limit switch 8 locates at a lower position, and is fixedly connected to the compression block 1 through a lower connecting plate; and the end limit switch 9 locates at an upper position, and is fixedly connected to the compression block 1 through an upper connecting plate. The upper connecting plate has a Q-shaped structure, and the end limit switch 9 locates at a top position of the Q-shaped structure to ensure a moving distance of the positioning bulge 32 between the start limit switch 8 and the end limit switch 9.

When the positioning bulge 32 contacts the start limit switch 8, a signal is sent from the start limit switch 8 to the central processing module 14, and the central processing module 14 sends out a signal to control the motor 5 to stop working; at this moment, the pressing plate mechanism locates at the lowest position; and when the positioning bulge 32 contacts the end limit switch 9, a signal is sent from the end limit switch 9 to the central processing module 14, and the central processing module 14 sends out a signal to control the motor 5 to stop working; at this moment, the pressing plate mechanism locates at the highest position.

The cooperation of the positioning bulge 32 with the start limit switch 8 and the end limit switch 9 achieves the controlling and limiting for the lifting of the support column 3.

In this embodiment, the detector 6 consists of two metal probes which are spaced with a small distance and arranged at a compression position at the bottom surface of the compression block. When a puncture site is bleeding, a micro short circuit is generated between the two metal probes; the detector 6 sends a signal to the central processing module 14; and the central processing module 14 sends out a signal to control the motor 5 to raise the support column, so that a gap between the tourniquet in the space from which the tourniquet passes of the compression mechanism and the tourniquet in the space from which the tourniquet passes of the pressing plate mechanism is increased. Due to a reaction force, the bleeding point is blocked by compression to achieve the hemostasis.

An installation case 7 is formed at an upper part of the middle channel of the pressing plate 2. The power supply module 11, the operation module and the central processing module 14 are located in the installation case 7.

The installation case of the pressing plate mechanism is further provided with a alarm buzzer 15. As the central processing module 14 sends out a signal to control the motor 5 to raise the support column 3, the central processing module 14 sends a signal to the alarm buzzer 15 to generate a buzz alarm to inform the medical staff.

A wire 17 for connecting the central processing module 14 and the transmission mechanism and a wire 17 for connecting the detector 6 and the central processing module 14 are wrapped around the support column 3 at the connecting sleeve to form a spring wire structure to avoid affecting the support column 3 to stretch.

The installation case 7 of the pressing plate mechanism is further provided with a time display module 16. A display screen of the time display module 16 is provided on a top cover 72 of the installation case 7 and is configured to display a hold time for compression. After the positioning bulge 32 contacts the end limit switch 9 to allow the pressing plate mechanism to locate at a highest position, the time display module 16 begins to time.

The compression block 1 is further provided with an indicator 18. When the intelligent femoral artery hemostasis device by compression works, the indicator 18 is on. The indicator 18 is a low-powered LED lamp, so that the indicator is avoided to generate heat.

The installation case 7 is further provided with an on-off module which is connected to the signal input end of the central processing module 14. An on-off button of the on-off module is partially provided outside the pressing plate mechanism for convenience of startup and shutdown.

The operation module includes a mainboard component 12 arranged in the pressing plate mechanism and a control contact 13 arranged on the mainboard component 12. A plurality of mainboard buttons are partially provided outside the pressing plate mechanism and are configured to cooperate with the control contact 13.

In this embodiment, the installation case 7 is formed by the top cover 72 and a lower casing 71 which are detachably connected; the lower casing 71 is fixedly connected to a lower part of the middle channel of the pressing plate 2; and the mainboard buttons of the operation module are provided on the top cover 72.

In this embodiment, the mainboard button includes a first mainboard button 121 for a manual mode and a second mainboard button 122 for an automatic mode.

In the manual mode, when the first mainboard button 121 is pressed, a signal is sent to the central processing module 14; the central processing module 14 sends out a signal to control the motor 5 to raise the support column 3; the support column 3 is raised to drive the pressing plate 2 to rise till the positioning bulge 32 contacts the end limit switch 9; a signal is sent from the end limit switch 9 to the central processing module 14; and the central processing module 14 sends out a signal to control the motor 5 to stop working. At this moment, the pressing plate mechanism locates at the highest position, the support column 3 stops rising, and the device is in a compression state. The first mainboard button 121 for the manual mode is pressed again to send a signal to the central processing module 14; the central processing module 14 sends out a signal to control the motor 5 to work reversely to drive the support column 3 to go down till the positioning bulge 32 contacts the start limit switch 8; a signal is sent from the start limit switch 8 to the central processing module 14; and the central processing module 14 sends out a signal to control the motor 5 to stop working. At this moment, the pressing plate mechanism locates at the lowest position, the support column 3 stops going down, and the device is in a decompression state.

When the second mainboard button 122 is pressed, i.e. in the automatic mode, the support column 3 is controlled to rise only according to the detecting signal from the detector 6. When the puncture site is bleeding, a micro short circuit is generated between the two metal probes; the detector 6 sends a signal to the central processing module 14; the central processing module 14 sends out a signal to control the motor 5 to raise the support column till the positioning bulge 32 contacts the end limit switch 9; a signal is sent from the end limit switch 9 to the central processing module 14; and the central processing module 14 sends out a signal to control the motor 5 to stop working. At this moment, the pressing plate mechanism locates at the highest position, the support column 3 stops rising, and the device is in a compression state. After holding for a period, the central processing module 14 sends out a signal to control the motor 5 to work reversely to drive the support column 3 to go down till the positioning bulge 32 contacts the start limit switch 8; a signal is sent from the start limit switch 8 to the central processing module 14; and the central processing module 14 sends out a signal to control the motor 5 to stop working. At this moment, the pressing plate mechanism locates at the lowest position, the support column 3 stops falling, and the device is in a decompression state.

This invention realizes automatic bleeding detection and automatic pressurizing, and ensures the integration and compactness of the intelligent femoral artery hemostasis device by compression. The power supply module, the operation module and the central processing module are integrated in the main body, avoiding external connecting wires and making it convenient to use the intelligent femoral artery hemostasis device by compression when the tourniquet works in a twining working condition.

The above is only some preferred embodiments of the present invention, and is not intended to limit the invention. Based on the detailed description for the invention in the above embodiments, modifications and equivalent substitutions may be made by those skilled in the art. It should be understood that any modification and local substitution within the spirit and principle of the invention shall fall into the scope of the invention.

In the description of the invention, it should be noted that directional terms, such as "upper", "lower", "front", "back", "left" and "right", indicate directions or positions based on the accompanying drawings, are merely for simplified description for the invention, and are not intended to indicate or imply specific directions, structures or operations of the referred device or component. Therefore, the directional terms herein should not be understood to limit the scope of the invention.

What is claimed is:

1. An intelligent femoral artery hemostasis device by compression, comprising a main body capable of automatic compression;

wherein the main body comprises a compression mechanism and a pressing plate mechanism successively provided from bottom to top; the compression mechanism and the pressing plate mechanism are separate structures; a support column is provided on the pressing plate mechanism and extends towards the compression mechanism; a lift regulator is provided between the support column and the compression mechanism and is configured to regulate the lifting of the support column; the lift regulator comprises a lift mechanism and a transmission mechanism which drives the movement of the lift mechanism; the compression mechanism is further provided with a detector for bleeding detection; and the main body is further integrated with a power supply module, an operation module and a central processing module; the detector and the operation module are respectively connected to a signal input end of the central processing module; and a signal output end of the central processing module is connected to the transmission mechanism of the lift regulator.

2. The intelligent femoral artery hemostasis device of claim 1, wherein the operation module comprises a mainboard component arranged in the pressing plate mechanism and a control contact arranged on the mainboard component; wherein a mainboard button is partially provided outside the pressing plate mechanism and is configured to cooperate with the control contact.

3. The intelligent femoral artery hemostasis device of claim 2, wherein the mainboard button comprises a first mainboard button for a manual mode and a second mainboard button for an automatic mode.

4. The intelligent femoral artery hemostasis device of claim 2, wherein the compression mechanism comprises a compression block, a space from which a tourniquet passes and a space from which a fixing band passes; the space from which the tourniquet passes and the space from which the fixing band passes are provided at the compression block, and the space from which the tourniquet passes is located above the space from which the fixing band passes;

an installation chamber is provided in the compression block; a bottom surface of the compression block is provided with a compression bulge; an upper side of the compression block is provided with a hole through which the support column passes; a connecting sleeve which protrudes upwardly is provided corresponding to the hole on the compression block; the support column passes through the connecting sleeve and is connected to the lift regulator; and the pressing plate mechanism comprises a pressing plate; and the pressing plate is connected to the support column and is provided with a space from which the tourniquet passes.

5. The intelligent femoral artery hemostasis device of claim 4, wherein the pressing plate is a flat sleeve; a middle channel of the flat sleeve forms the space from which the tourniquet passes; an installation case is formed at an upper part of the middle channel of the pressing plate; and the power supply module, the operation module and the central processing module are located in the installation case.

6. The intelligent femoral artery hemostasis device of claim 5, wherein the installation case is formed by a top cover and a lower casing which are detachably connected; the lower casing is fixedly connected to a lower part of the middle channel; and the mainboard button of the operation module is provided on the top cover.

7. The intelligent femoral artery hemostasis device of claim 5, wherein the lift mechanism comprises an inner threaded hole arranged at an axis of the support column and a stud matching and arranged in the inner threaded hole, wherein a lower end of the stud is connected to the transmission mechanism;

the support column has a non-circular section, so that the support column cooperates with the hole to achieve a circumferential rotation limit for the support column;

a positioning bulge is further provided on the support column; a start limit switch and an end limit switch are provided corresponding to the positioning bulge in the installation chamber; the start limit switch and the end limit switch are respectively connected to the signal input end of the central processing module;

when the positioning bulge contacts the start limit switch, a signal is sent from the start limit switch to the central processing module, and the central processing module sends out a signal to control the transmission mechanism to stop working; at this moment, the pressing plate mechanism locates at a lowest position; and when the positioning bulge contacts the end limit switch, a signal is sent from the end limit switch to the central processing module, and the central processing module sends out a signal to control the transmission mechanism to stop working; and at this moment, the pressing plate mechanism locates at a highest position.

8. The intelligent femoral artery hemostasis device of claim 5, wherein the installation case in the pressing plate mechanism is further provided with an alarm; and the detector comprises two metal probes which are spaced and arranged at a compression position at the bottom surface of the compression block; and wherein when a puncture site is bleeding, a micro short circuit is configured to be generated between the two metal probes, the detector sends a signal to the central processing module, the central processing module sends out a signal to control the transmission mechanism to raise the support column, and the central processing module sends a signal to the alarm.

9. The intelligent femoral artery hemostasis device of claim 5, wherein the installation case of the pressing plate mechanism is further provided with a time display module, and a display screen of the time display module is provided on the top cover of the installation case.

10. The intelligent femoral artery hemostasis device of claim 5, wherein a wire for connecting the central processing module and the transmission mechanism and a wire for connecting the central processing module and the detector are wrapped around the support column at the connecting sleeve to form a spring wire structure.

* * * * *